United States Patent [19]
Leupold et al.

[11] Patent Number: 5,230,804
[45] Date of Patent: Jul. 27, 1993

[54] PROCESS FOR SEPARATING CATALYSTS FROM SUSPENSIONS BY FILTRATION

[75] Inventors: Ernst I. Leupold, Neu-Anspach; Eduard Zeisberger, Hattersheim am Main; Manfred Kauffelt, Frankfurt am Main; Willi Herzog, Sulzbach; Udo Dettmeier; Georg Weichselbaumer, both of Kelkheim, all of Fed. Rep. of Germany

[73] Assignee: Hoechst AG, Frankfurt am Main, Fed. Rep. of Germany

[21] Appl. No.: 852,797

[22] Filed: Mar. 17, 1992

[30] Foreign Application Priority Data

Mar. 19, 1991 [DE] Fed. Rep. of Germany ....... 4108870

[51] Int. Cl.$^5$ ............................................. B01D 61/00
[52] U.S. Cl. .................................... 210/651; 210/653; 210/649; 210/636
[58] Field of Search .............. 210/767, 649, 653, 651, 210/503, 509, 500.25, 636, 510.1; 423/22, 140

[56] References Cited

U.S. PATENT DOCUMENTS

| | | | |
|---|---|---|---|
| 3,617,553 | 11/1971 | Westaway et al. | 210/651 |
| 4,136,025 | 1/1979 | Zwack et al. | 210/636 |
| 4,311,521 | 1/1982 | Harper et al. | 423/140 |
| 4,312,778 | 1/1982 | Harper | 423/140 |
| 5,102,632 | 4/1992 | Allen et al. | 423/22 |

FOREIGN PATENT DOCUMENTS

0206054 10/1989 European Pat. Off. .
2936123C2 4/1987 Fed. Rep. of Germany .

Primary Examiner—Robert A. Dawson
Assistant Examiner—Ana M. Fortuna
Attorney, Agent, or Firm—Connolly and Hutz

[57] ABSTRACT

The process for separating off rare metal catalysts used in the preparation of ether-carboxylic acids by catalytic oxidation with a suspended catalyst comprises carrying out a crossflow filtration and pretreating the filter elements used with a medium which is not solid under the treatment conditions and is composed of one or more carboxylic acids.

12 Claims, 1 Drawing Sheet

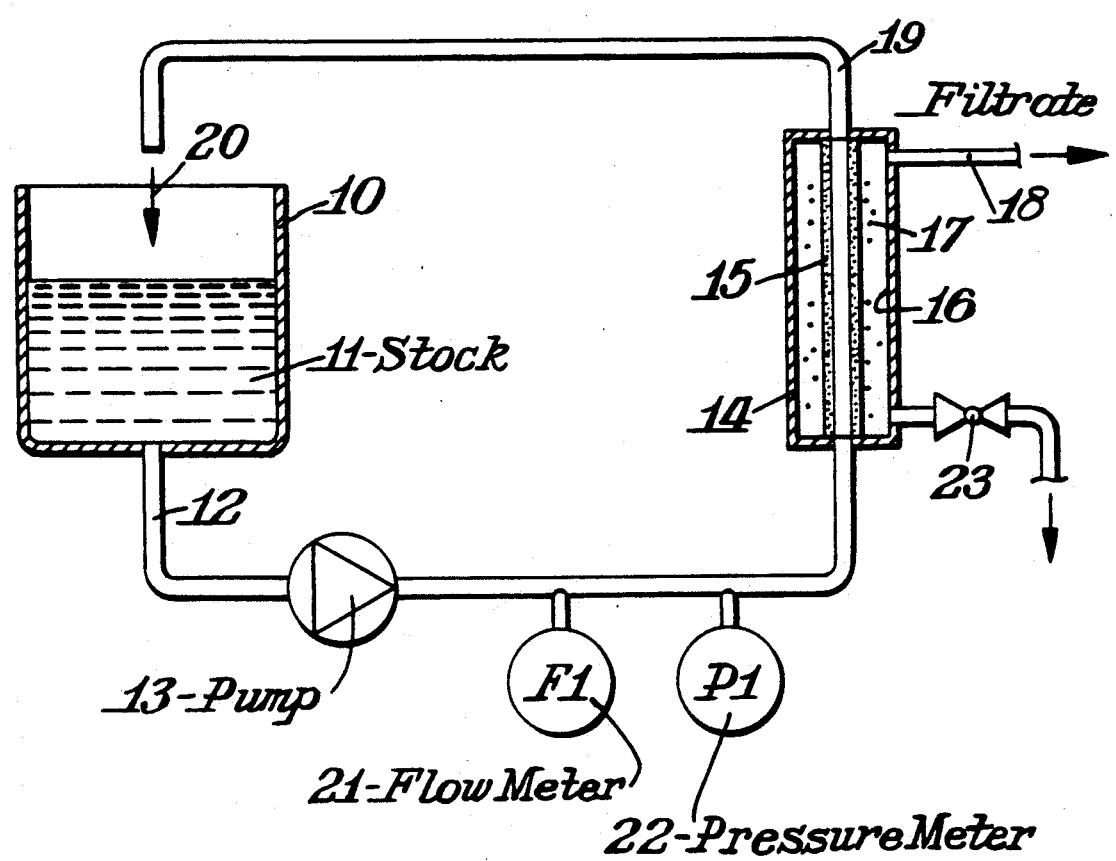

PROCESS FOR SEPARATING CATALYSTS FROM SUSPENSIONS BY FILTRATION

DESCRIPTION

Process for separating catalysts from suspensions by filtration.

INTRODUCTION

The present invention relates to a process for separating off suspended rare metal catalysts used in the preparation of ether-carboxylic acids by catalytic oxidation of the corresponding ether-alcohols with oxygen, by filtration.

BACKGROUND OF THE INVENTION

The catalytic oxidation of ether-alcohols according to the equation

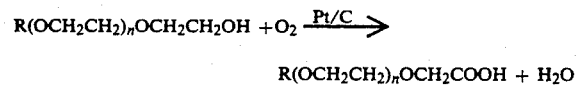

$$R(OCH_2CH_2)_nOCH_2CH_2OH + O_2 \xrightarrow{Pt/C}$$
$$R(OCH_2CH_2)_nOCH_2COOH + H_2O$$

has been known for a considerable time and has been described, for example, in German Patent 2,936,123 and European Patent 206,054. With increasing molecular mass of the radical R, however, the separation and hence the complete recovery and recycling of the rare metal catalyst becomes more difficult.

It was therefore the object to develop a technically and economically acceptable process for separating catalysts from suspensions by filtration.

SUMMARY OF THE INVENTION

The present invention relates to a process for separating off rare metal catalysts used in the preparation of ether-carboxylic acids by catalytic oxidation with a suspended catalyst, which comprises carrying out a crossflow filtration and subjecting the filter elements used to a pretreatment and, if necessary, an intermediate treatment with a medium which is not solid under the treatment conditions and is composed of one or more carboxylic acids.

In the crossflow filtration, the catalyst-containing reaction mixture is pumped at a high overflow velocity tangentially to the membrane surface through the filter element, the filtrate being discharged through the membrane layer transversely to the direction of flow, as is described in detail in Ullmann's Encyclopedia of Industrial Chemistry, 5th Edition, volume B2, pages 10-54.

Tubular filter elements having a membrane layer on the inside of the tubes are particularly suitable. Preferred membrane and carrier materials are ceramic materials, $\alpha$-$Al_2O_3$ and/or $ZrO_2$. Plastic elements and carbon elements can also be used. The membrane and carrier can be composed of different materials. The necessary pore sizes are expediently in the range usual for ultrafiltration, for example between about 1 and about 200 nm. A suitable apparatus is described in the example (in this connection, cf. FIG. 1).

BRIEF DESCRIPTION OF THE FIGURE

The FIGURE is a diagram illustrating the apparatus used in the process of this invention.

These and other objects will be understood in the light of the following description taken together with the drawing.

DESCRIPTION OF AN EMBODIMENT

The FIGURE shows an embodiment for carrying out the method of the invention. A tank 10 represents a source for a solution 11 obtained in the catalytic oxidation of the ether-carboxylic acid with a suspended catalyst. The solution 11 is moved through a pipeline 12 by a pump 13 to a housing 14 which contains a filter element 15. The filter element 15 is centrally positioned within the housing 14 to provide a chamber 16 within the housing 11 and adjacent the filter element 15. The flow of the solution as illustrated in the FIGURE is upward through the element 15 and the housing 14 so that the solution moves tangentially to the filter element 15 and a filtrate 17 is discharged transversely through the filter element 15. The filtrate 17 is removed from the chamber 16 through a discharge conduit 18. A pipeline 19 from the upper side of housing 11 receives a catalyst concentrate 20 from the filter element 15. The concentrate 20 is recycled.

A flow meter 21 and a pressure meter 22 are provided to monitor the flow of the solution 11. A valve 23 is provided as a means for draining the chamber 16.

DETAILED DESCRIPTION

In the treatment, according to the invention, of the filter element 15, the latter is expediently immersed into the liquid carboxylic acid. This can be effected, for example, by directly filling the filter housing 14 with the acid, or in a separate vessel after dismantling of the filter. The treatment is naturally carried out before the filtration step and advantageously is repeated at certain intervals after a prolonged operating period. However, a repetition, which can be carried out, for example, after about 30 to 100 filtrations, is not absolutely necessary but it can safeguard the performance capacity over a prolonged period in the case of extreme filtration conditions.

Suitable carboxylic acids are especially those of the formula R—COOH, where R is a linear or branched hydrocarbon radical having 1 to 18 carbon atoms, which can be substituted by hydroxyl, alkoxy, carboxyl or halogen, such as fluorine, chlorine, bromine or iodine, or aryl, alkyl($C_1$-$C_9$)aryl or arylalkyl, for example the benzyl radical, where the aryl can in each case contain 6 to 16 carbon atoms, such as phenyl, naphthyl or biphenyl radicals, and can be substituted by the said substituents. In general, however, any carboxylic acids or mixtures or solutions of carboxylic acids are suitable, which are in the liquid form at the temperature at which the treatment of the filter element is carried out, especially aliphatic and aromatic compounds such as formic acid, acetic acid, propionic acid, isovaleric acid, n-dodecanoic acid, benzoic acid and phenylacetic acid. However, unsaturated, substituted or polybasic carboxylic acids, such as glycolic acid, methoxyacetic acid, chloroacetic acid, lactic acid, crotonic acid and maleic acid, can also be used. As a result of the easy availability and ease of handling, acetic acid is preferred.

The treatment according to the invention is in general carried out at an elevated temperature, preferably between about 30° and 250° C., and particularly preferably between about 40° and 160° C. However, satisfactory results are also still obtained outside these limits.

The treatment time is in general selected such that at least one complete permeation of the filter is achieved. In general, a treatment time from 0.5 to 50 hours, especially 1 to 10 hours, is sufficient. Working under an elevated pressure, for example at 1 to 10 bar, is not necessary, but it can lead to a shortening of the required treatment period because of the more rapid permeation of the filter. An extension of the treatment time, for example during a plant shutdown, over several days or weeks does not adversely affect the effectiveness of the filterability. The treatment can also be carried out with carboxylic acids in the form of vapor, for example by passing vapor over the filter.

Surprisingly, the process according to the invention solves the problem of the gradual decrease in the performance of the filter elements 15 during filtration, which occurs, for example, in the filtration of long-chain ether-carboxylic acids, above all of those having surfactant properties, by a technically simple measure.

EXAMPLE

A solution, such as is obtained in the catalytic oxidation of ether-carboxylic acids with a suspended catalyst, composed of 25% by weight of ether-carboxylic acid of the formula R—$(OCH_2CH_2)_n OCH_2COOH$, in which R represents linear alkyl groups having a distribution from $C_{12}$ to $C_{14}$ and n has a mean value of 4, and also 60% by weight of diethylene glycol dimethyl ether, 15% by weight of water and 5% by weight of a suspended commercially available catalyst (5% by weight of platinum on activated carbon), is treated with hydrogen for 30 minutes at 80° C. in a bubble column and then subjected to a crossflow filtration. Before use, the filter element is immersed in acetic acid for 8 hours at 70° C. and then washed with water. It consists of an $Al_2O_3$ tube (diameter: 7 mm, length: 250 mm), the inside of the tube being a membrane layer with pore sizes of 100 nm ($10^{-9}$ m). An apparatus according to FIG. 1 is used. The solution is pumped at a linear flow velocity of 5 m/second through the filter element 15 located in a housing 14. A pressure $P_1$ of 1.5 bar is set at a temperature of 70° C. The filtrate then flows at a rate of 2.0 l/hour. Concentrating of the catalyst up to a solids content of about 30% by weight is achieved. This concentrate is recycled into the catalytic oxidation. The clear filtrate passes to further processing. Even after 200 filtrations with about 2000 l of filtrate, no decrease in the filtrate flow is observed. After every 50 filtrations, an intermediate treatment (acetic acid, 2 hours, 70° C.) is carried out.

We claim:

1. A process for separating a catalyst from a solution obtained in the catalytic oxidation of ether-alcohols to produce ether carboxylic acid with a suspended catalyst, the process comprising the steps of:

treating a porous filter element by permeating the element with one or more carboxylic acids in an amount to maintain flow through said element;
   contacting the ether carboxylic acid with the suspended catalyst solution with said filter element;
   discharging a filtrate through said filter element transversely of the passage of the solution; and
   collecting a catalyst concentrate.

2. The process as claimed in claim 1, wherein the carboxylic acid used is acetic acid.

3. The process as claimed in claim 1, wherein the filter element is subjected to an intermediate treatment with one or more carboxylic acids.

4. The process as claimed in claim 3, wherein the intermediate treatment is carried out after about 30 to 100 filtrations.

5. The process as claimed in claim 1, wherein the filter elements are composed of a ceramic material and/or carbon.

6. The process as claimed in claim 1, wherein the filter element is composed of $ZrO_2$ and/or $\alpha$-$Al_2O_3$.

7. In the process as claimed in claim 1, wherein in said step of treating the filter element, the carboxylic acid is a carboxylic acid according to the following structural formula

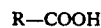

R—COOH wherein
   R denotes a linear or branched hydrocarbon radical having 1 to 18 carbon atoms, unsubstituted or substituted by hydroxyl, alkoxy, carboxyl or halogen, or aryl, alkyl ($C_1$-$C_9$)aryl or arylalkyl groups in which in each case the aryl group contains 6 to 16 carbon atoms and is unsubstituted or substituted by hydroxyl, alkoxy, carboxyl or halogen, or aryl, alkyl ($C_1$-$C_9$)aryl or arylalkyl groups.

8. The process as claimed in claim 1, wherein the filter element is treated by immersion in the liquid carboxylic acid for 0.5 to 50 hours.

9. The process as claimed in claim 8, wherein the filter element is treated by immersion in the liquid carboxylic acid for 1–10 hours.

10. The process as claimed in claim 1, in which the treatment is carried out at an elevated temperature.

11. The process as claimed in claim 10, wherein the temperature is between 30° and 250° C.

12. The process as claimed in claim 11, wherein the temperature is between 40°-160° C.

* * * * *